United States Patent [19]

Feigelson

[11] 4,252,799
[45] Feb. 24, 1981

[54] TREATMENT OF MALE ANIMAL PERINATES WITH MALE SEX HORMONE

[76] Inventor: Muriel Feigelson, 265 Tenafly Rd., Tenafly, N.J. 07670

[21] Appl. No.: 32,732

[22] Filed: Apr. 24, 1979

[51] Int. Cl.³ .......................................... A61K 31/56
[52] U.S. Cl. ................................................ 424/243
[58] Field of Search ..................................... 424/243

[56] References Cited

PUBLICATIONS

Chem. Abstracts (1977) (vol. 86), Par. 134056g.
"Androgens," by Dorfman et al., (1956), Wiley & Sons, New York, pp. 158-168.

*Primary Examiner*—Elbert L. Roberts

*Attorney, Agent, or Firm*—Cooper, Dunham, Clark, Griffin & Moran

[57] ABSTRACT

In accordance with the present invention it has been found that administration of a male sex hormone such as an androgen to a male animal perinate, particularly a male mammal neonate, suppresses subsequent masculine sexual development, particularly testicular development. Postnatal testicular growth, development of androgen secretion and circulating luteinizing and follicle stimulating hormone levels in castrated adults are all markedly diminished. This androgenic effect does not require aromatization to estrogen. Testes and adenohypophyses of treated rats are competent to respond to exogenous gonadotropins and gonadotropin releasing hormone, respectively.

5 Claims, 2 Drawing Figures

TREATMENT OF MALE ANIMAL PERINATES WITH MALE SEX HORMONE

The invention described herein was made in the course of work under Grant Number HD08712-04 from the Department of Health, Education and Welfare.

BACKGROUND OF THE INVENTION

U.S. Pat. No. 2,824,546 discloses that natural follicle hormones may be utilized for fattening cattle, hogs, and other domestic animals, for hormonal castration of domestic animals, especially male animals, such as boars, steers, cockerels and the like, and for various other veterinary purposes. More particularly, U.S. Pat. No. 2,824,546 teaches that natural follicle hormone preparations when administered to male animals will enhance fattening of the animal if the hormones are administered about three months before the animal is to be slaughtered.

Differentiation of the rodent brain during the neonatal period, which results in sexual dimorphism, has been extensively investigated previously. (See for example, Barraclough, C. A., *Endocrinology* 68, 62 (1961); Barraclough, C. A. and Gorski, R. A., *Endocrinology*, 68, 68 (1961); Harris, G. W. and Levine, S., *J. Physiol.*, 163, 42 (1962); and Barraclough, C. A., *Endocrinology* 78, 1053 (1966).) Experiments involving castration of male, or androgenization of female, neonates have demonstrated that androgen, which is normally secreted by the male gonad during the neonatal period and probably aromatized to estrogen within neural tissues (Reddy, V.V.R., et al, *Endocrinology* 94, 117 (1974); Weisz, J. and Gibbs, C., *Neuroendocrinology*, 14, 72 (1974); and Lieberburg, T. and McEwen, B. S., *Brain Res.*, 85, 165 (1975)) suppresses hypothalmic positive feedback control centers and thus cyclic gonadotropin secretion (Mennin, S. P. and Gorski, R. A., *Endocrinology*, 96, 486 (1975) and Harlan, R. E. and Gorski, R. A., *Endocrinology*, 101, 741 (1977)).

Less attention has been focused on investigation of the development of tonic gonadotropin secretion, which may be conveniently studied in the male, in whom complexities due to cyclicity are reduced. We report here a developmental event, occurring during the perinatal period, which is necessary for normal subsequent tonic gonadotropin secretion and consequent testicular maturation. The existence of this event has been demonstrated by inhibiting testicular development in male mammals by administering pharmacologically effective doses of androgen.

SUMMARY OF THE INVENTION

The present invention provides a method of treating a male animal, particularly a male mammal perinate to prevent subsequent testicular development and sexual maturation. Specifically, it has been found that administration to a perinate male animal of an amount of male sex hormone such as an androgen above about 0.1 mg per gram of body weight is effective to inhibit subsequent testicular development and sexual maturation. The administration of androgen may be accomplished in various ways, including subcutaneous injection, intravenous injection, intramuscular injection, and/or oral ingestion. For the treatment of mammals particularly effective male sex hormones are androgens including testosterone propionate and 5α-dihydrotestosterone propionate as well as testosterone and 5α-dihydrotestosterone.

In accordance with the present invention, it has been found that administration of a male sex hormone such as an androgen is effective in inhibiting subsequent testicular development and sexual maturation only if administered during the perinatal period which would include administration to perinatal animals in the final trimester prior to birth and extend to neonatal males up to about 6 days after birth. However, particularly preferred is a period from about 3 days prior to birth up to about 3 days after birth.

Thus, in accordance with the teachings of the present invention, a method of hormonal castration has been provided which comprises administering to a male animal perinate an amount of a male sex hormone such as an androgen effective to inhibit testicular development during subsequent maturation of the animal. Although experiments described hereinafter concern male rats, it would be obvious to one skilled in the art that the teachings of the present invention have applicability to the wide range of animals which produce sex hormones. Thus as used herein the term "animal" includes numerous animals such as dogs, cats, steers, boars, horses, camels, sheep, bison, lions, tigers, deer, reindeer, goats, whales, rats, mice, birds including cockerels and insects.

For some of the animals the teachings of the present invention provide a method of improving the quality and tenderness of the animal's meat. For others the present invention provides a method of inhibiting their sexual development and thus rendering them sterile.

DETAILED DESCRIPTION OF THE INVENTION 1.75 mg/day of testosterone propionate (TP) has been administered to intact male rats on days one (day of birth) and two of life. A marked suppression of postnatal testicular growth and development of androgen secretion, as monitored by seminal vesicle and ventral prostate weights, was observed. At 63 days of age, testes, seminal vesicle and ventral prostate weights of males treated neonatally with TP were, respectively, 36, 11, and 19 percent of diluent injected controls. Histological examination of the adult testes of these neonatally androgenized rats revealed seminiferous tubular lumena devoid of mature spermatazoa. All treated males were infertile. Moreover, when the same dose of the non-aromatizable androgen, 5α-dihydrotestosterone propionate (DHTP), was administered neonatally, a more variable, but even more profound, impairment of testicular growth and development of androgen secretory function was noted. Mean weights of testes, seminal vesicles and ventral prostates of DHTP treated rats at 63 days were, respectively, 14, 7 and 11 percent of controls. Thus, unlike neonatal suppression of gonadotropic cyclicity and ovulation in the female, where conversion of androgen to entrogen within the brain has been implicated, impairment of testicular growth and function in the neonatal male by androgen does not require aromatization to estrogen.

Figure 1:
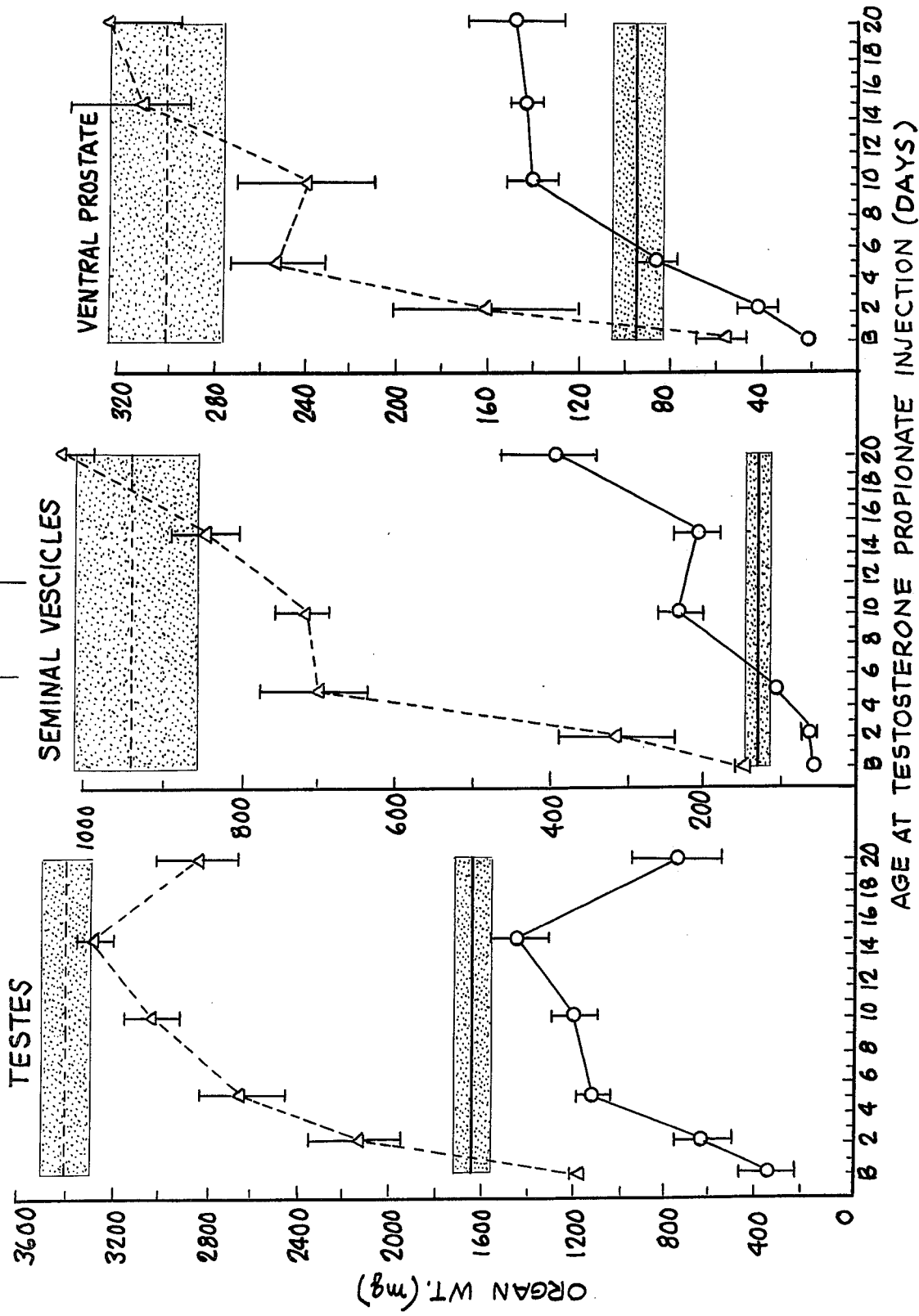
FIG. 1 depicts the neonatal period during which androgen administration is capable of suppressing subsequent testicular development and androgen secretion, as monitored by seminal vesicle and ventral prostate weights. A single dose of 2.5 mg TP/10 g body weight was injected, s.c., at the ages indicated on the abscissa (day of birth=0 days of age). Weights of testes, seminal vesicles and ventral prostates of animals killed at 41 (o—o) and 64 (Δ—Δ) days are plotted as means ±SEM (vertical bars); control lines depict means±SEM (strippled area) of organ weights of rats killed at 41 (—) and 64 (—) days, in which sesame oil was injected at various ages corresponding to those receiving TP.

Further distinctions between suppression of the development of cyclicity in the neonatally androgenized female and inhibition of subsequent testicular development in the neonatally androgenized male, observed in this study are: (a) effective androgen dose and (b) duration of the androgen vulnerable perinatal period. As shown in Table I a single dose of 50 μg TP administered to female neonates is sufficient to induce an anovulatory, and thus sterile, adult female. In contrast, at least 500 μg TP, administered as a single dose on the day of birth, is required to significantly impair testicular and accessory sex organ development in the male. One hundred percent infertility at adulthood requires yet higher androgen doses. The anovulatory syndrome may be elicited by treatment of the neonatal female up to 10 days of age, whereas the vulnerable neonatal period for testicular suppression is more restricted. FIG. 1 illustrates that a single injection of 2.5 mg TP per 10 g body weight, administered only up until 2 days of age (first three neonatal days), evokes marked reductions in testes, seminal vesicle and ventral prostate weights at 41 and 64 days. Androgen treatment at 5 days of age results in modest suppressive effects on male sex organ development comparable to those noted by previous investigators (Barraclough, C. A. and Leatham, J. H., *Anat. Rec.*, 134, 239 (1959); Swanson, H. E. and van der Werff ten Bosch, J. J., *Acta Edocrinol.* (Kbh.) 47, 37 (1964); Johnson, D. C., et al, *J. Endocrinol.* 29, 95 (1964); and Kincl, F. A., et al, *Acta Endocrinol.* (Kbh.) 49, 193 (1965). Sexual development in the male is no longer impaired by androgen treatment at 10 days of age. A direct effect of exogenous TP administered at 20 days may be seen both at 41 and 64 days in FIG. 1, namely, hypertrophy of seminal vesicles and ventral prostate, accompanied by a feedback inhibition of testicular development. Indeed, a direct hypertrophic effect on accessory sex organs of 41 day old rats is seen following androgen administration from 10 days of age onwards.

TABLE I

EFFECTS OF NEONATAL ANDROGEN ADMINISTRATION ON FERTILITY

| Neonatal TP (mg) | | | |
|---|---|---|---|
| M | × | F | Fertiltiy |
| 0 | | 0 | at 72 days  6/6 |
| 0.05 | | 0 | 6/6 |
| 0 | | 0.05 | 0/6 |
| 0.10 | | 0 | 6/6 |
| 0.50 | | 0 | 3/5 |
| 1.75 | | 0 | 1/5 |
| 0 | | 0 | at 112 days  6/6 |
| 1.75 | | 0 | 3/6 |
| 3.50 (1.75 × 2) | | 0 | 0/4 |

Investigation of the mechanisms by which androgen administered to the early neonate suppresses testicular development has been initiated. Testes of neonatally androgenized males were shown to be competent to respond to prepuberal administration of gonadotropins by exhibiting precocious increases in their growth rate and androgen secretion. Thus, the testes is not the primary site of lesion induced by neonatal androgenization.

The effects of neonatal androgenization on the development of tonic gonadotropin secretion by the anterior pituitary were also explored. It may be seen in FIG. 2 that levels of circulating radioimmunoassayable luteinizing hormone (LH) and follicle stimulating hormone (FSH) of normal neonatally TP treated intact adult males are comparable. However, a reduction in feedback suppression of gonadotropin secretion and an increase in the sensitivity of the pituitary to LH releasing hormone (LHRH) would be expected in adult males which had been neonatally androgenized due to their reduced levels of testicular androgen secretion. To obviate these variables, normal and neonatally androgenized males were castrated 16 days prior to collection of sera at 65 days of age. The elevations in serum LH and FSH following castration of non-androgenized adults are readily apparent in FIG. 2. Of particular significance, however, is the 75–80% reduction of serum LH and FSH concentrations in the castrated adults which were neonatally androgenized. Thus, as revealed in the castrated adult, whose pituitary is unopposed by endogeneous androgen secretion, neonatal androgenization inhibits normal development of tonic secretion of gonadotropins. These findings, which are based on radioimmunoassay of the individual gonadotropins, are consistent with those of Kurcz and coworkers (Kurcz, M. and Gerhardt, V. J., *Endocrinol. Exper.*, 2, 29 (1968), and Kurcz, M., et al, *Acta Biol. Acad. Sci. Hung.* 20, 389 (1969). These workers measured circulating combined gonadotropins by bioassay in neonatally androgenized castrated adult males.

Figure 2:
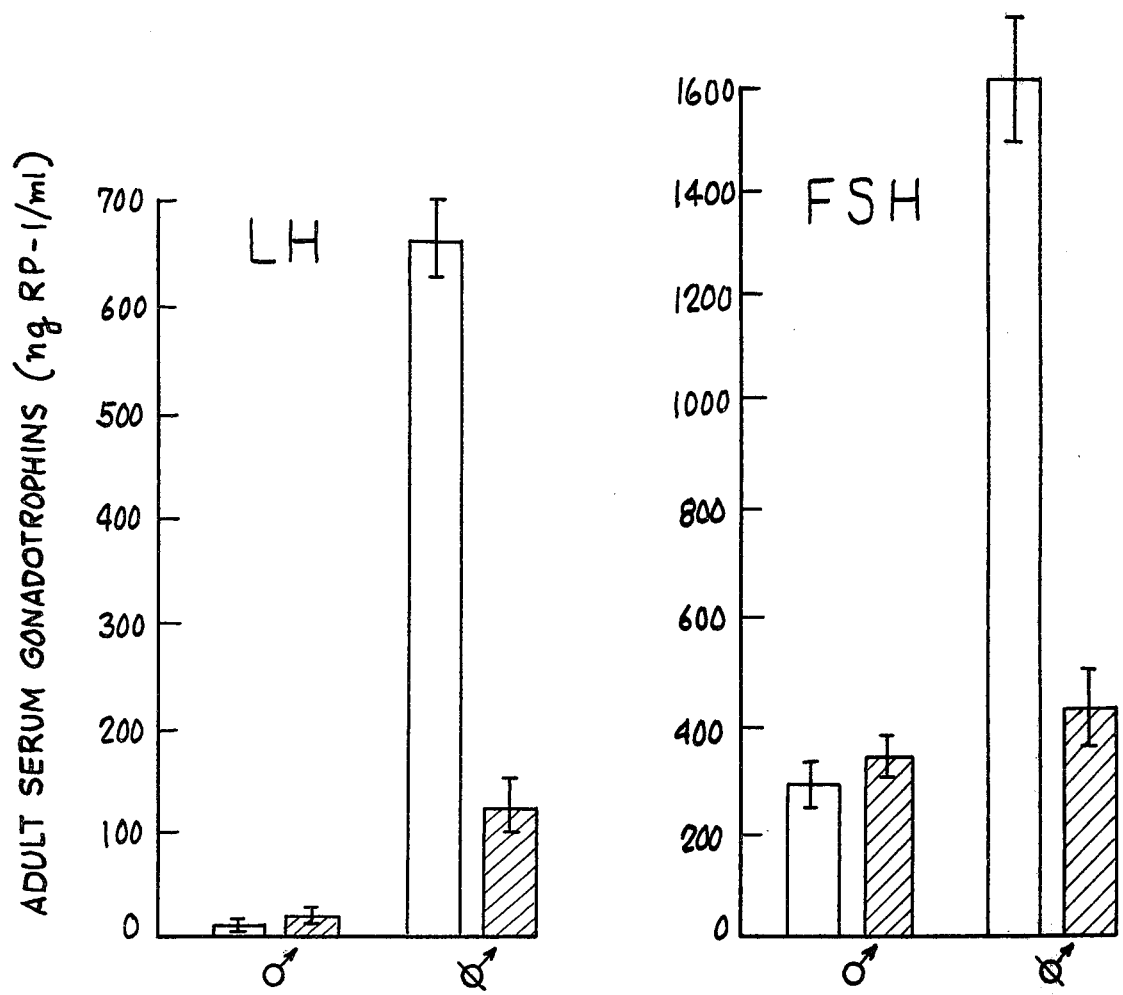
FIG. 2 illustrates the effects of neonatal androgenization on serum radioimmunoassayable LH and FSH in intact and castrated adult males. Sesame oil (open bars) and 1.75 mg TP/day in sesame oil (hatched bars) were injected, s.c., on days 1 and 2 of life. Rats were bilaterally castrated on day 49 and killed by decapitation on day 64. Trunk blood was collected and sera were assayed for LH and FSH by radioimmunoassay (Midgely, A. R., Jr., et al, *Rec. Prog. Hormone Res.* 27, 735 (1971)) using rat LH-RP-1 and rat FSH-PR-1 as standards.

As with the acyclic pituitaries of neonatally androgenized females, (Mennin, S. P., et al, *Endocrinology* 95, 412 (1974)) pituitaries of neonatally androgenized castrated adult males secrete LH in response to exogenous gonadotropin releasing hormone (LHRH) (Table II), although their tonic gonadotropin secretion is markedly impaired (as shown in FIG. 2). Increases in whole blood LH concentrations were elicited in both androgenized and non-androgenized castrated males twenty minutes following challenge with 1 μg LHRH intravenously; respectively, five- and ten-fold elevations in non-androgenized and neonatally and androgenized castrated males were observed. However, absolute increases in blood LH levels following LHRH administration to neonatally androgenized castrated males, whose baseline levels were suppressed, were less than controls, namely, 169 and 385 ng/ml, respectively. It is concluded from these observations that the primary site of lesion induced by neonatal androgenization of the male is not at the level of the pituitary, but rather may be at hypothalamic or higher brain centers. The smaller absolute increase in LH secretion in response to exogenous LHRH, observed in these neonatally androgenized rats, may be secondary to long term diminished hypophyseal stimulation by endogenous LHRH over the two month developmental period.

TABLE II

Effect of neonatal androgenization on the competence of pituitaries of adult castrated male rats to elicit elevations in circulating LH following challenge with LHRH. Control and neonatally androgenized rats were administered sesame oil and 1.75 mg testosterone propionate, respectively, on days 1 (birth) and 2, castrated on day 49. On day 65, LH was assayed by radioimmunoassay in whole heparinized tail blood prior to, and 20 minutes following, intra-jugular injection of 1 $\mu$g LHRH. Blood LH concentrations are expressed as means $\pm$SEM.

| Treatment | Blood LH (ng RP-1/ml) | |
|---|---|---|
| | Prior to LHRH | 20 min after LHRH |
| Control | 125 $\pm$ 42 | 508 $\pm$ 52 |
| Neonatal androgen | 19 $\pm$ 6 | 188 $\pm$ 19 |

These findings are compatible with with the following working hypothesis. A developmental event, suppressible by pharmacological doses of androgen, occurs during the first few postpartum days in hypothalamic or higher neural centers of the male. This event, which is responsible for the development of tonic gonadotropin secretion and resultant testicular maturation, is to be distinguished from neonatal differentiation of the cyclic hypothalamic centers, which results from suppression by physiological levels of androgen normally secreted by the male neonate. Whether the developmental event which underlies the observation we have described constitutes: (a) actual biochemical and/or morphological developmental changes in the tonic neural centers of the neonate, or (b) a state of transient vulnerability of these centers to exogenous androgen, remains to be clarified.

This invention additionally provides a method of improving the quality of meat derived from slaughtered animals which comprises administering to said animals during the perinatal period of their development an amount of a male sex hormone effective to prevent subsequent testicular development and sexual maturation.

Finally, this invention provides a method of combatting rodents and/or insects including rats, mice, roaches and the like which comprises administering to said rodents and/or insects an amount of a male sex hormone effective to inhibit subsequent sexual maturation, said administration being during the perinatal period of development of said rodents or insects.

As will be obvious to one skilled in the art, many modifications, variations, or alterations may be made in the practices of this invention without departing from the spirit or scope thereof as set forth in the preceding description or in the claims which follow.

What is claimed is:

1. A method of treating male animals of the type normally slaughtered at adulthood to obtain meat suitable for human consumption so as to improve the quality of the meat derived from the slaughtered adult animal which comprises administering to such a male animal solely during its perinatal period an amount of a male sex hormone effective to inhibit subsequent testicular development and sexual maturation upon growth of the animal to adulthood, allowing the thus-treated animal to grow to maturity and then slaughtering the treated animal to recover meat of improved quality therefrom.

2. A method in accordance with claim 1 wherein said male animal is selected from the group consisting of steers, boars, sheep, bison, goats, deer and camels.

3. A method in accordance with claim 1 wherein said male sex hormone is an androgen, said effective amount is an amount above about 0.1 mg/g of body weight of said animal and said perinatal period extends up to about 3 days after birth.

4. A method in accordance with claim 3 wherein said androgen is testosterone propionate.

5. A method in accordance with claim 3 wherein said androgen is 5α-dihydrotestosterone propionate.

* * * * *